United States Patent
Soetermans

(10) Patent No.: US 8,490,235 B2
(45) Date of Patent: Jul. 23, 2013

(54) ENDOSCOPE-CLEANING DEVICE

(75) Inventor: Maximiliano Soetermans, Pinnacle, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 877 days.

(21) Appl. No.: 12/444,666

(22) PCT Filed: Oct. 9, 2007

(86) PCT No.: PCT/US2007/080806
§ 371 (c)(1),
(2), (4) Date: Nov. 23, 2009

(87) PCT Pub. No.: WO2008/048823
PCT Pub. Date: Apr. 24, 2008

(65) Prior Publication Data
US 2010/0065083 A1    Mar. 18, 2010

Related U.S. Application Data

(60) Provisional application No. 60/852,382, filed on Oct. 17, 2006.

(51) Int. Cl.
*A61B 1/00* (2006.01)

(52) U.S. Cl.
USPC .................................. 15/104.16; 15/104.05

(58) Field of Classification Search
USPC .............................. 15/104.05, 104.03, 104.16
See application file for complete search history.

(56) References Cited

U.S. PATENT DOCUMENTS

| | | | |
|---|---|---|---|
| 5,407,423 A * | 4/1995 | Yoon | 604/1 |
| 5,514,085 A | 5/1996 | Yoon | |
| 6,699,331 B1 | 3/2004 | Kritzler | |
| 2004/0187893 A1* | 9/2004 | Maguire et al. | 134/8 |

FOREIGN PATENT DOCUMENTS

| | | | |
|---|---|---|---|
| DE | 43 05 118 C1 | | 3/1994 |
| JP | 8-173380 | * | 7/1994 |
| JP | 2006 051057 A | | 2/2006 |
| JP | 2006051057 A | * | 2/2006 |

OTHER PUBLICATIONS

*Endoscope Cleaning Guide*, by Olympus (product brochure, Aug. 2003).
*Rainbow Endoscopic Cleaning Brush*, (product advertisement) http://www.cookgroup.com/wiison_cook/International/pages/int09.html (2006).
*Disposable Endoscopic Cleaning Brush*, http://www.scopex.com/pages/prod-divine.shtml, product advertisement (2004).
*Disposable Endoscopic Cleaning Brushes*, Cook Endoscopy brochure (Jan. 2006).
*Cleaning Brushes: Disposable*, (product advertisement) http://www.hobbsmedical.com/ProductSpecs.asp?nProductID=5 (2006).

* cited by examiner

*Primary Examiner* — Laura C Guidotti
(74) *Attorney, Agent, or Firm* — Brinks Hofer Gilson & Lione

(57) ABSTRACT

A device and method for cleaning a channel of an endoscope, the device including a flexible elongate body (102) with a sponge (104) disposed adjacent one end and optionally including a lumen (108) and openings (106) for directing a cleaning fluid through the elongate body.

6 Claims, 3 Drawing Sheets ously, the sponge most preferably provides cavities or spaces within its body and/or between adjacent sponge surfaces, which spaces are configured to capture debris dislodged from the endoscope channel.

ENDOSCOPE-CLEANING DEVICE

CROSS-REFERENCE TO RELATED APPLICATIONS

This application is filed under 35 U.S.C. §371 based upon PCT App. Ser. No. PCT/US2007/80806 filed Oct. 9, 2007 (and published as WO/2008/048823 on Apr. 24, 2008) designating the United States and published in English, which application claims priority under 35 U.S.C. §119 to U.S. Provisional Application Ser. No. 60/852,382, filed Oct. 17, 2006. Each of the foregoing applications is incorporated herein by reference in its entirety.

FIELD OF THE INVENTION

The present invention relates generally to a cleaning device for use with medical devices, and more specifically to a cleaning device for cleaning endoscopes. In particular, the present invention relates to a device for cleaning one or more lumens of an endoscope such as, for example, a duodenoscope.

BACKGROUND

During use in surgical procedures, an endoscope typically becomes soiled with biological and other materials from a patient body (e.g., biliary fluids, saliva, feces, blood, pieces of tissue, etc.) and potentially from other devices or materials used in conjunction with the endoscope. Because endoscopes are used multiple times, it is important that they are completely cleaned between uses to avoid cross-contamination between devices used with them, and between different patients.

A typical cleaning regimen for cleansing of an endoscope includes wiping it down with a detergent (such as an enzymatic detergent), then soaking it in and flushing it with a same or different detergent, water, and air, and then finally drying it. The detergent provides for chemical cleaning and the flushing provides for mechanical cleaning.

Some mechanical aids are known for use in cleaning the inner channels of an endoscope, including the main working channel and other channels (e.g., accessory channels used for suction and/or passage of air or water, which collectively are referred to herein as endoscope channels or lumens). For example, several companies make linear and tapered brushes that have bristles projecting from a central shaft to provide mechanical abrasion to the lumenal surfaces in an endoscope. As another example, U.S. Pat. No. 6,699,331 to Kritzler discloses a sponge device for spreading lumenal contamination of an endoscope into a substantially uniform film on the lumenal surface so that enzymatic cleaners can more efficiently and uniformly digest the contaminating material.

However, each of these devices has some shortcomings. Because of their rigidity and shape, bristles of brush devices do not provide uniform contact with the endoscope's lumenal surfaces. The sponge device of Kritzler is not configured to provide the mechanical force/contact needed to actually remove adhering lumenal contaminants, but rather spreads them uniformly. As a result, there still exists a need for a device that overcomes these shortcomings and provides for both mechanical and chemical cleaning of endoscope lumens.

BRIEF SUMMARY

In one aspect, the present invention includes a sponge-comprising device for cleaning wherein the device is configured to be deployed through an endoscope lumen such as, for example, a working channel, to contact and aid in removal of material therefrom. In another aspect, the present invention includes methods for cleaning an endoscope using a device including a sponge.

DETAILED DESCRIPTION

Figure 1:
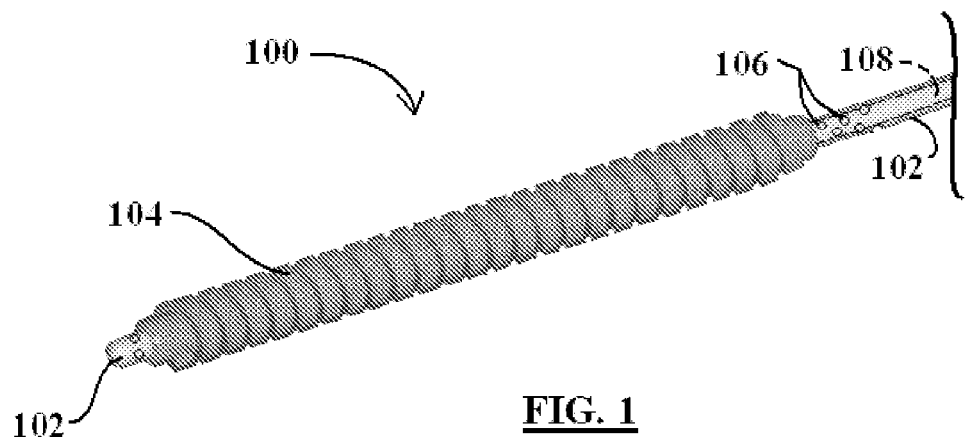
FIG. 1 depicts a first embodiment of a device for cleaning an endoscope.

FIG. 1 illustrates one embodiment of a endoscope-cleaning device 100. The device 100 includes an elongate body with a flexible, axially actuatable shaft 102 forming its major length. The shaft 102 is depicted as a catheter, but may alternatively be embodied as a solid shaft. A cleaning sponge 104 having a ridged/grooved external surface is disposed near the distal end of the device 100. The cleaning sponge can comprise any number of shape configurations, but most preferably provides substantial surface area configured for contacting the lumenal surface of an endoscope. Additionally, the sponge most preferably provides cavities or spaces within its body and/or between adjacent sponge surfaces, which spaces are configured to capture debris dislodged from the endoscope channel.

Figure 1A:
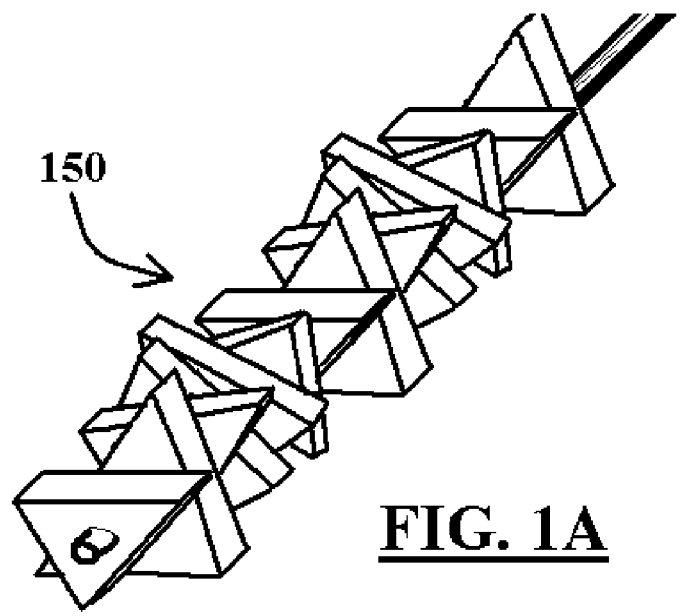
FIG. 1A illustrates in top perspective view a sponge embodiment having a "periodic triangular cross-section"
Figure 1B:
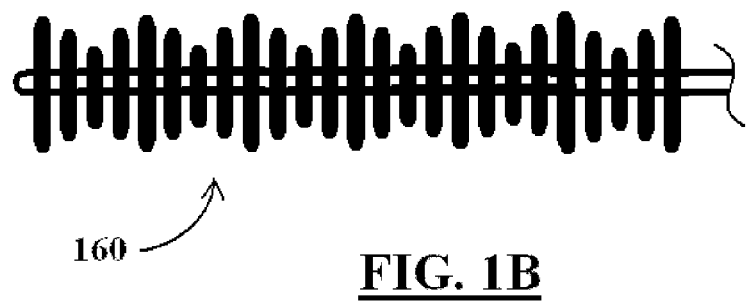
FIG. 1B depicts another sponge embodiment, having alternating disks of varying diameter.
Figure 1C:
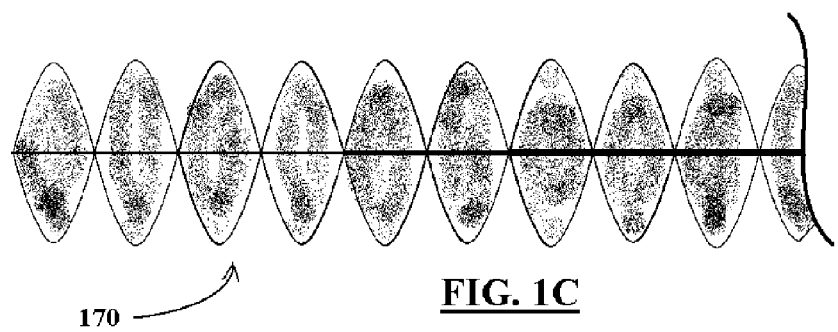
FIG. 1C shows another sponge embodiment having a generally sinusoidal profile

By way of example of sponges with alternative geometries: FIG. 1A illustrates in top perspective view a sponge 150 having "periodic triangular cross-section" wherein the sponge includes a series of offset triangular sections; FIG. 1B depicts a sponge 160 having alternating disks of varying diameter; and FIG. 1C shows a sponge 170 having a generally dual-sinusoidal side profile (each of the sponge segments having a generally elliptical cross-section). Those of skill in the art will appreciate that other sponge configurations providing the abrasive lumenal surface contact to remove and collect debris may be used within the scope of the present invention.

The shaft 102 includes optional openings 106 through the shaft wall, which are preferably both adjacent to and underneath (not shown) the sponge 104. The openings 106 are in fluid communication with a central lumen 108 that extends longitudinally through the shaft 102 and provide for passage of fluid (e.g., detergent, air, water) therethrough during a cleaning operation using the device 100. Supplying a fluid such as a cleaning agent during the mechanical contact of the sponge with a lumenal surface of an endoscope preferably provides a rinsing action. The outer diameter of the sponge 104 preferably is the same as, or—more preferably—is slightly larger than, the inner diameter of the endoscope lumen to be cleaned in order to provide an increased amount of surface friction for cleanly dislodging material from the lumenal surface.

A method of cleaning using the device 100 may include the following steps: (1) Flushing the endoscope channel to be cleaned with water and/or an enzymatic detergent; (2) Inserting the endoscope-cleaning device 100 into the endoscope channel; (3) Moving the shaft 102 of the device 100 axially so that the sponge 104 travels along at least a portion of the channel (which may include moving the device 100 axially in a reciprocating manner to effect a scrubbing action, moving the device 100 axially from one end of the channel to the other, and/or rotating the device 100 about its longitudinal axis to effect a scrubbing action); (4) Directing an enzymatic detergent through the shaft 102 and out the openings 106; and, (5) Directing sterile water through the shaft 102 and out the opening 106. In an alternative method useful for an embodiment of the device 100 with or without the openings 106, a fluid may be introduced to the endoscope channel before or during actuation of the device 100 therein, the sponge 104 may be dipped or soaked in a fluid prior to its introduction to the channel, and/or the device 100 may be introduced into the channel while the endoscope is at least partially submerged in a fluid bath.

As described above, a sponge 104 of the present device may include a variety of sponge configurations, but preferably is an open-cell polymer sponge (e.g., polypropylene). A preferred sponge maintains sufficient cellular rigidity to provide abrasive mechanical force against the lumenal wall of an endoscope channel while providing for effective delivery of cleaning solution. Said effective delivery includes by passage through the sponge from openings in the shaft on which the sponge is mounted if such openings are provided, and also includes effective carrying of solution when the sponge is dipped into a fluid before being placed into the endoscope channel. A shaft 102 of the present device may be formed of a metal (such as, for example, hypotube), but preferably is formed of a polymer. The shaft may be solid, or may include a central channel with one or more openings provided for passage of a fluid therethrough. In a device having a shaft provided with such openings, the sponge may cover the openings and allow passage of a fluid through the sponge material, and/or the sponge may be disposed along the shaft in a pattern (e.g., helical coil) where the openings are exposed to an outer non-sponge-covered surface.

Figure 2A:
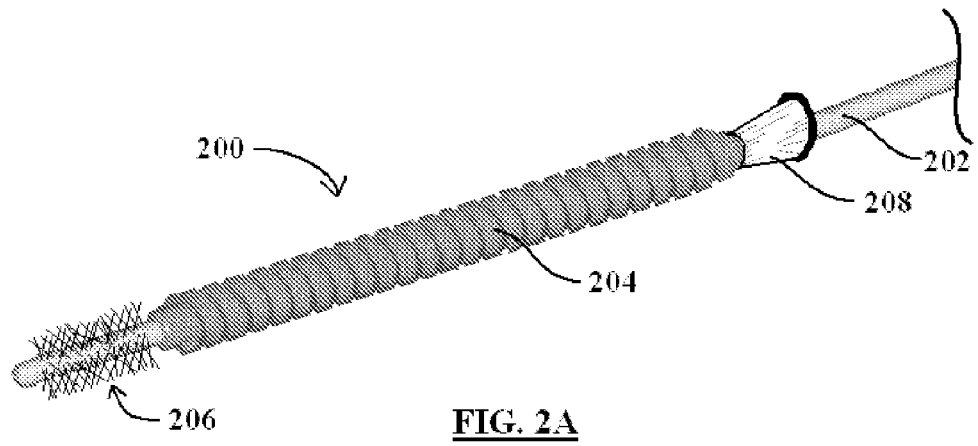
FIG. 2A depicts a second embodiment of a device for cleaning an endoscope.

FIG. 2A shows a second embodiment of a catheter cleaning device 200. The second device embodiment 200 includes an elongate body, with a flexible, axially actuatable shaft 202 forming its major length. The shaft 202 is depicted as a solid shaft, but optionally may be a catheter with a lumen therethrough allowing for passage of, for example, a cleaning solution—with or without side openings in the shaft. A cleaning sponge 204 formed as a helix around the shaft 202 is disposed near the distal end of the device 200. The cleaning sponge can comprise any number of shape configurations, but most preferably provides a substantial surface area configured for contacting the lumenal surface of an endoscope. The outer diameter of the sponge 204 preferably is the same as, or—more preferably—is slightly larger than, the inner diameter of the endoscope lumen to be cleaned in order to provide an increased amount of surface friction for cleanly dislodging material from the lumenal surface. A bristled brush surface 206 is disposed on the shaft distal of and adjacent to the sponge 204. A semi-flexible conical wiper 208 is disposed on the shaft proximal of and adjacent to the sponge 204.

The second device embodiment 200 preferably is used for a cleaning operation in a "push mode." Specifically, the shaft 202 is provided with a length sufficient to push the distal cleaning end all the way through a channel of an endoscope. The device 200 may be pushed straight through, or—preferably—may be rotated about its longitudinal axis while being advanced through the endoscope. The device preferably is not pulled proximally for any significant length during a cleaning operation. For any of the devices described above, those of skill in the art will appreciate that the proximal/distal orientations described above may be changed without departing from the scope of the present invention.

In a preferred method of use for the second device embodiment, cleaning fluid solution such as a detergent and/or enzymatic solution is provided in the endoscope channel to be cleaned. The fluid may be provided by immersing the endoscope into a bath, pouring or injecting fluid directly through the channel, and/or by directing fluid through the device shaft. As the device is advanced—distal cleaning end first—through the channel, the distal/leading brush provides a stiff plurality of mechanically abrasive surfaces to dislodge contaminants, the adjacent/following sponge provides a scrubbing action with a variegated surface to enhance the removal of contaminants adhering to the lumenal wall of the endoscope channel, and the trailing conical wiper provides a wiping action to "squeegee" away any loose material not picked up by the sponge. In a preferred embodiment of this method, the channel is also thereafter flushed with cleaning solution and sterile water. The device 200 may be configured such that the major length of the shaft can be drawn through the endoscope channel after the cleaning end is pushed out, or such that the cleaning end may be removed and the major shaft length withdrawn through the end from which it was introduced. The latter option will be useful if a larger handle is provided at the proximal shaft end for manipulating the shaft during a cleaning operation.

Figure 2B:
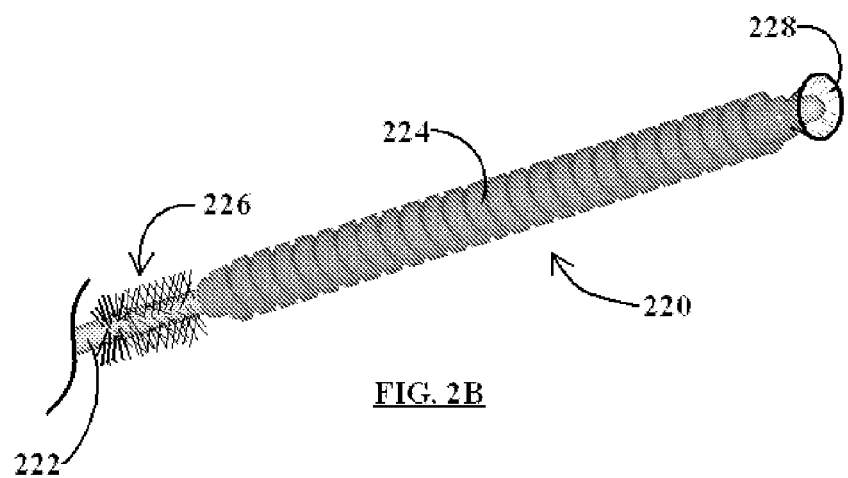
FIG. 2B depicts a third embodiment of a device for cleaning an endoscope.

FIG. 2B shows a third embodiment of a catheter cleaning device 220. The third device embodiment 220 includes an elongate body, with a flexible, axially actuatable shaft 222 forming its major length. The shaft 222 is depicted as a solid shaft, but optionally may be a catheter with a lumen therethrough allowing for passage of, for example, a cleaning solution—with or without side openings in the shaft. A cleaning sponge 224 formed as a helix around the shaft 222 is disposed near the distal end of the device 220. The cleaning sponge can comprise any number of shape configurations, but most preferably provides a substantial surface area configured for contacting the lumenal surface of an endoscope. The outer diameter of the sponge 224 preferably is the same as, or—more preferably—is slightly larger than, the inner diameter of the endoscope lumen to be cleaned in order to provide an increased amount of surface friction for cleanly dislodging material from the lumenal surface. A bristled brush surface 226 is disposed on the shaft proximal of and adjacent the sponge 224. A semi-flexible conical wiper 228 is disposed on the shaft distal of and adjacent the sponge 224.

The third device embodiment 220 preferably is used for a cleaning operation in a "pull mode." Specifically, the shaft 222 is provided with a length sufficient to pull the distal cleaning end all the way through a channel of an endoscope. The device 220 may be pulled straight through, or—preferably—may be rotated about its longitudinal axis while being drawn through the endoscope. The device preferably is not pushed distally for any significant length during a cleaning operation.

In a preferred method of use for the third device embodiment, cleaning fluid solution such as a detergent and/or enzymatic solution is provided in the endoscope channel to be cleaned. The fluid may be provided by immersing the endoscope into a bath, pouring or injecting fluid directly through the channel, and/or by directing fluid through the device shaft. The shaft is pushed through the channel until it can be grasped and pulled from the opposite end. Alternatively, the cleaning end (comprising wiper, sponge, and brush on a shaft portion) may be separate from a major shaft length and attachable thereto (e.g., by a threaded or bayonet connection) after the shaft is directed through the endoscope channel to be cleaned. As the device is drawn through the channel, the proximal/leading brush provides a stiff plurality of mechanically abrasive surfaces to dislodge contaminants, the adjacent/following sponge provides a scrubbing action with a variegated surface to enhance the removal of contaminants adhering to the lumenal wall of the endoscope channel, and the distal/trailing conical wiper provides a wiping action to "squeegee" away any loose material not picked up by the sponge. In a preferred embodiment of this method, the channel is also thereafter flushed with cleaning solution and sterile water.

It is intended that the foregoing detailed description be regarded as illustrative rather than limiting, and it should be understood that the following claims, including all equivalents, are intended to define the spirit and scope of this invention.

I claim:

1. A device for cleaning an endoscope, the device comprising:
   a flexible elongate body having a first end and a second end, and having a sponge member being disposed adjacent the second end, the body traversing the entire length of an endoscope channel;
   wherein an outer diameter of said elongate body and sponge is such that the elongate body and sponge member when passing through the endoscope channel with the sponge member maintains a frictional contact with a surface of the endoscope channel, said frictional contact being sufficient to substantially remove a deposited material from the surface;
   wherein the elongate body comprises a catheter body having a lumen extending longitudinally therethrough and one or more openings providing fluid communication from the lumen to an exterior surface of the catheter body; and
   further comprising a brush member disposed adjacent to an end of the sponge member.

2. The device of claim 1, wherein the one or more openings provide a path for fluid communication from the lumen to the sponge member.

3. The device of claim 1, wherein the one or more openings provide a path for fluid communication from the lumen to the exterior surface adjacent the sponge member.

4. The device of claim 1, further comprising a wiper member disposed adjacent to an end of the sponge member.

5. The device of claim 4, wherein the wiper member and brush member are disposed adjacent opposite ends of the sponge member.

6. The device of claim 4, wherein the wiper member and brush member are disposed adjacent a same end of the sponge member.

\* \* \* \* \*

UNITED STATES PATENT AND TRADEMARK OFFICE
CERTIFICATE OF CORRECTION

PATENT NO.       : 8,490,235 B2
APPLICATION NO. : 12/444666
DATED            : July 23, 2013
INVENTOR(S)      : Maximiliano Soetermans Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1097 days.

Signed and Sealed this
Eighth Day of September, 2015

Michelle K. Lee
*Director of the United States Patent and Trademark Office*